United States Patent
Kimura et al.

(10) Patent No.: US 8,116,857 B2
(45) Date of Patent: Feb. 14, 2012

(54) NON-LINEAR SIGNAL SEPARATION METHOD USING NON-LINEAR STATE SPACE PROJECTION METHOD

(75) Inventors: Yoshitaka Kimura, Sendai (JP); Shinichi Chida, Sendai (JP); Mitsuyuki Nakao, Sendai (JP); Kunihiro Okamura, Sendai (JP); Takuya Ito, Sendai (JP)

(73) Assignee: Tohoku University, Sendai-shi (JP)

( * ) Notice: Subject to any disclaimer, the term of this patent is extended or adjusted under 35 U.S.C. 154(b) by 889 days.

(21) Appl. No.: 12/065,645

(22) PCT Filed: Aug. 22, 2006

(86) PCT No.: PCT/JP2006/316386
§ 371 (c)(1),
(2), (4) Date: May 9, 2008

(87) PCT Pub. No.: WO2007/029485
PCT Pub. Date: Mar. 15, 2007

(65) Prior Publication Data
US 2009/0270713 A1 Oct. 29, 2009

(30) Foreign Application Priority Data
Sep. 5, 2005 (JP) .................... 2005-256300

(51) Int. Cl.
*A61B 5/0444* (2006.01)
(52) U.S. Cl. ....................................... 600/511
(58) Field of Classification Search .................. 600/511
See application file for complete search history.

(56) References Cited

U.S. PATENT DOCUMENTS
2004/0260169 A1* 12/2004 Sternnickel .................. 600/409

FOREIGN PATENT DOCUMENTS
JP  2002 538872   11/2002
WO  2006 080167   8/2006

OTHER PUBLICATIONS

Matsuyama, Fumiaki et al., "Extraction of fetal ECG from mother's abdominal electrical signals", IEICE Technical Report, vol. 105, No. 402, pp. 25-28, (2005), (with English abstract).
Richter, Marcus et al., "Fetal ECG Extraction with Nonlinear State-Space Projections", IEEE Transactions on Biomedical Engineering, vol. 45, No. 1, pp. 133-137, (1998).
Sato, Michiyoshi et al., "Extraction of Fetal Electrocardiogram by Blind Source Separation", Technical Report of IEICE, vol. 104, No. 429, pp. 45-48, (2004), (with English abstract).

* cited by examiner

*Primary Examiner* — Kennedy Schaetzle
(74) *Attorney, Agent, or Firm* — Oblon, Spivak, McClelland, Maier & Neustadt, L.L.P.

(57) ABSTRACT

There is provided a non-linear signal separation method using the non-linear state space projection method capable of separating an effective non-linear signal even if the S/N ratio is low by performing the time domain high speed non-linear state space projection when a signal is a multi-channel signal and has a periodicity. In the non-linear signal separation method using the non-linear state space projection method, an original signal having a complex signal which is a multi-channel and cyclic signal measured from one phenomenon is processed by using the time domain high-speed non-linear state space projection method so as to estimate a noise in the original signal and subtract the estimated noise from the original signal, thereby separating the signal to be measured in the original signal as a non-linear signal even when the S/N ratio is low.

10 Claims, 5 Drawing Sheets

NON-LINEAR SIGNAL SEPARATION METHOD USING NON-LINEAR STATE SPACE PROJECTION METHOD

TECHNICAL FIELD

The present invention relates to the non-linear separation method by using non-linear state space projection method, or more particularly, relates to the separation method of a biological signal to detect an electrocardiogram of a fetus from a childbearing mother's body.

BACKGROUND ART

Conventionally, one of the noninvasive and passive methods of extracting an electrocardiogram from a fetus is a method of extracting an fetal electrocardiogram signal by using adaptive signal processing filters (See Patent Document 1 described in the following.).

However, it is difficult to extract signals effectively by using this method when the S/N ratio becomes low, as in the cases where noise components suddenly change due to a fetus movement, contraction of an uterus, a movement of a mother's body, or oppositely go up and down very slowly, or fat components (vernix caseosa) increase around a fetus in the pregnancy period from 26 weeks to 36 weeks, making it difficult to detect a fetal electrocardiogram signal.

The present inventors have already proposed an independent component analysis (ICA) method using a reference system and applied for a patent (Patent Document 2 described below.). This method is a processing method to extract only a fetal electrocardiogram from a signal superposed by an electrocardiogram signal, an electromyogram signal and the like of a mother's body. This ICA method is a method of extracting a signal intensity having a high correlation with a reference system signal on the basis of independency of a signal component. By using a signal having approximate frequency as a reference signal, a signal having frequency approximate to reference frequency can be extracted. Furthermore, since this method is to extract a signal from a distributed profile, a signal can be extracted even when there is data having frequency remote from the cycle of a reference system or data is missing. In addition, an allorhythmic pulse can be found from these data.

Here a description is given to a standard electrocardiogram and names are given to each part of a waveform.

FIG. 1 shows a basic waveform of an electrocardiogram.

In this figure, P wave is a wave resulting from propagation of the action potential through the atrium heart. QRS wave is a wave resulting from generation of the action potential in the ventricular muscle. T wave is a wave resulting from extinction of the action potential of the heart ventricle. U wave indicates a wave whose origin and the others are not clear. Measurement of the electrocardiogram provides various information concerning the activity of the heart. For example, time duration from P to R (PR duration) corresponds to the propagation time of stimulation from the atrium heart to the heart ventricle (atrioventricular conduction time). Furthermore, measurement of the electrocardiogram is a powerful means for medical diagnosis because it provides electrocardiograms peculiar to various diseases. It is indispensable for diagnosis of the allorhythmic pulse, and a peculiar change in the ST part is well known for the ischemic disease.

Although the ICA method can surely extract the R component which is the characteristic of the fetal electrocardiogram component, it is difficult to extract components P, Q, S, T necessary for the electrocardiogram signal by using only this method. It is therefore important to combine this method with a means to remove a noise.

The means to remove a noise is (1) separating signals based on the distribution thereof in the case of the ICA method, (2) removing a noise by a linear prediction using a FIR filter in the case of active noise cancellation (ANC) (3) Wavelet filter represented by Wavelet Packet, FFT analysis using the Fourier transform, and other bandpass filters and the like in the case of using filters, and (4) extracting a chaos orbit from a noise, which is derived from the chaos analysis, in the case of the non-linear state space projection method (NSSP: Non-linear State Space Projection).

The ANC, FFT, and Wavelet filter described above are linear transformation methods, and therefore, after removal of noise, all signals including a necessary signal becomes dull. Even the processing in the frequency domain using the Wavelet transformation method has some effects of the noise treatment on over all signals because it is a linear transformation method. Furthermore, there is a drawback in the linear transformation method that it cannot reconstruct the dynamic system. Due to these situations, a non-linear transformation method NSSP is considered to be a candidate.

As described in Patent Document 2 in the following, the ICA is used to extract data with S/N ratio less than 1 from the original signal.

As described in Non-Patent Document 1 in the following, the NSSP method generates data shifted a little bit (by 4 msec) on the time axis from the original signal which contains a mixture of the electrocardiogram signal and the electromyogram signal from the mother's body and the fetus. This process is repeated 11 times, thereby making data of 11 dimensions. A Lorentz plot is made by cutting vertically along the time axis, wherein the original signal and the signal shifted 11 times are put into X and Y, respectively.

At this time, the orbit of the plotted data repeatedly takes approximately the same route (Since this orbit is not linear, the method is called non-linear.). Then, the scatter of the data between each cycle is measured within the plane by defining a plane perpendicular to the direction in which the orbit passes. Then, the scatter of the data within the plane (noise) is calculated by using the principal component analysis method. The signal is obtained by removing a noise.

This method was derived originally from the property of the state space in the chaos dynamics, and as a non-linear signal processing technique, various applications are considered such as separating the measured noise from the chaos orbit and separating a noise from the electrocardiogram. Advantageously, this method makes it possible to analyze a signal even from a single channel, and also to deal with non-linearly mixed signals on the state space. This method also enables non-linear signal processing which can not be accomplished by using the conventional linear filtering method based on the frequency analysis such as FFT and Wavelet analysis.

[Patent Document 1]: Published Japanese Translations of PCT International Publication for Patent Application 2002-538872.

[Patent Document 2]: Japanese Patent Application 2005-023982.

[Non-Patent Document 1] M. Richter, T. Schreiber, and D. T. Kaplan. Fetal ECG Extraction with Nonlinear State-Space Projections. IEEE Trans. Biomed. Eng., Vol. 45, 1998, pp. 133-137.

[Non-Patent Document 2] L. D. Lathauwer, B. D. Moor, and J. Vandewall, Fetal Electrocardiogram Extraction by Blind Source Subspace Separation. IEEE Trans. Biomed. Eng., Vol. 47, 2000, pp. 567-572.

[Non-Patent Document 3] V. Zarzoso and A. K. Nandi, Non-invasive Fetal Electrocardiogram Extraction: Blind Separation Versus Adaptive Noise Cancellation. IEEE Trans. Biomed. Eng., Vol. 48, 2001, pp. 12-18.

[Non-Patent Document 4] M. O. Taylor, M. J. Smith, M. Thomas, A. R. Green, F. Cheng, Oseku-Afful S, Wee L Y, Fisk N M and Gardiner H M, Noninvasive fetal electrocardiography in singleton and multiple pregnancies. BJOG Aol. 110, 2003, pp. 668-678.

[Non-Patent Document 5] M. G. Jafari, and A. C. Chamber, Fetal Electrocardiogram Extraction by Sequential Source Separation in the Wavelet Domain, IEEE Trans. Biomed. Eng., Vol. 52, 2005, pp. 390-400.

[Non-Patent Document 6] M. Sato, Y. Kimura, M. Nakano, N. Katayama, Extraction of Fetal Electrocardiogram by Blind Source Separation, MBE 2004-63, 2004, pp. 45-48.

DISCLOSURE OF INVENTION

However, the NSSP method described above has various drawbacks as described in the following.

(1) Many calculations must be performed. Multiple data group comprising original data and data time-shifted from the original data by a given time interval is stored and a principal component analysis is performed at each point. This procedure takes a long time. For example, it takes as long as 6 hours of calculation time to carry out a data analysis only for 5 seconds when a conventional calculator (a commercially available personal computer) is used. It takes at least 3 minutes even when the present inventers adopt a method to thin out the calculation interval without deteriorating the calculation accuracy, therefore, it is difficult to do an on-line measurement by using this method.

(2) When there is wide scatter in the data, it is not possible to realize good accuracy in calculation.

Since the data shifted from each other are put into Lorentz plot in the NSSP method, there is high risk for data other than the target trajectory point group to mix into the data when the data contains a large amount of scatter. For this reason, removal of a noise can be made only for an original signal with less amount of scatter. Furthermore, the NSSP method is applicable to analysis on condition that there is a difference between a main signal intensity and a noise intensity, a main signal and a noise signal (i.e. a main signal and a noise can be discriminated markedly).

In other words, when applying the NSSP method to practical problems, a neighborhood must be defined so that intersection of the objective dynamic trajectories at each point of the measurement signal trajectory in the state space can be prevented from occurring. Hence it is necessary to ensure sufficient dimension for practical measurements with complicated variations. Therefore the calculation speed is significantly reduced, which makes it difficult to use this method in general analysis. In addition, when white noise component is included, it is impossible in principle to find a low dimensional neighborhood which dose not have intersecting property, no matter how the dimension is increased, since this noise has in principle an infinite dimension. In particular, when a S/N ratio is low, these drawbacks become severe and tend to limit the quality of signal to be analyzed in practice.

By taking the situation described above into account, the purpose of the present invention is to provide non-linear signal separation method using non-linear state space projection method capable of separating a non-linear signal effectively even in a case of low S/N ratio by performing the time domain high-speed non-linear state space projection method to a multi-channel and cyclic signal.

Since the conventional NSSP method shifts in time sequence data obtained from a phenomenon and sets a state space as a virtual multi-dimensional space, numbers of points increase as dimensions increase. Due to this, the NSSP method needs to extend the dimension sufficiently to avoid intersection of the trajectory in the state space, and inevitably calculation time increase significantly in order to realize accurate calculate. In addition, since the temporal information in the state space is limited to a narrow region of the number of dimension, a restoration of a non-linear structure with much longer time is impossible, and remains in a neighborhood of the linear filtering region.

The present invention, on the other hand, sets the state space by making use of the stable periodicity, and therefore performs calculation to the data while keeping the number of data as same as the number of data obtained from a phenomenon, thereby enabling rapid calculation. Furthermore, since the present invention can use all of the temporal information of the stable, periodical signal, the non-linear structure of the phenomenon can be restored within the repetitive period of the obtained phenomenon.

Thus the present invention has such features none of the non-linear filtering in the art discloses, and is a novel noise reduction method in principle.

The essential aspect of the present invention in the case of a multiple and cyclic data is (1) shifting cyclic data by one cycle to superpose on the original one. This process is carried out up to several cycles until the summation average becomes stable, for example up to 10 cycles or more. (2) Summation averages are calculated by the superposed data. (3) Scatter from the average is plotted (here, in one dimension). (4) Data processing is carried out in another channel according to the procedure (1) to (3) described above. (5) The processed data for all channels are plotted as a multi-dimensional figure. (6) Calculation is performed to obtain a noise at each data point by performing the principal component analysis for the scatter of noise in the multi-dimensional plane at each time. (7) Removing the calculated noise from the original data to obtain the signal. The procedures (3) and (4) described above is performed to obtain deviation from probability distribution.

Since the method of the present invention performs NSSP in time domain, and can perform data processing with high speed, it can be called time domain high-speed non-linear state space projection method (Fast Non-linear State Space Projection in time domain; FNSSP in TD).

In the following, descriptions will be given on the inventive parts and their features of the present invention more particularly.

(1) The non-linear signal separation method using non-linear state space projection method is characterized in that an original signal having a complex signal which is a multi-channel and cyclic signal measured from one phenomenon is processed by using the time domain high-speed non-linear state space projection method so as to estimate a noise in the original signal and subtract the estimated noise from the original signal, thereby separating the signal to be measured in the original signal as a non-linear signal even when S/N ratio is low.

(2) The non-linear signal separation method using non-linear state space projection method in the above [1] is characterized in that the cyclic signal to be measured is a biological signal.

(3) The non-linear signal separation method using non-linear state space projection method in the above [2] is characterized in that the biological signal is an electrocardiogram signal.

(4) The non-linear signal separation method using non-linear state space projection method in the above [3] is characterized in that the electrocardiogram signal is an electrocardiogram signal of a fetus in a mother's body.

(5) The non-linear signal separation method using non-linear state space projection method in the above [4] is characterized in that the original signal is processed by using the first time domain high-speed non-linear state space projection method so as to remove the electrocardiogram signal of mother's body, the signal with the electrocardiogram signal of the mother's body removed therefrom is processed by the second time domain high-speed non-linear state space projection method so as to remove the noise signal, thereby obtaining the electrocardiogram signal of the fetus.

(6) The non-linear signal separation method using non-linear state space projection method in the above [2] is characterized in that the biological signal is a functional MRI signal.

(7) The non-linear signal separation method using non-linear state space projection method in the above [2] is characterized in that the biological signal is a brain wave signal.

(8) The non-linear signal separation method using non-linear state space projection method in the above [1] is characterized in that the cyclic signal to be measured is a technological measurement signal.

(9) The non-linear signal separation method using non-linear state space projection method in the above [8] is characterized in that the technological measurement signal is a defective sound signal of a rotating machine included in a normal rotating sound signal of the rotating machine.

The method of the present invention is a improved version of the NSSP method, and when the state space including the temporal axis is formed, the method becomes free from the limitation of the neighborhood, because no recurrent characteristics is present in the direction of the time axis. Furthermore, a time domain high-speed non-linear state space projection method (FNSSP in TD) has been developed as a new signal separation technology based on this principle, which reduces the processing time to less than 1/30 to 1/100 of that of the conventional non-linear state space projection method (NSSP method). This reduction enables an on-line measurement.

BEST MODE FOR CARRYING OUT THE INVENTION

The non-linear signal separation method using the non-linear state space projection method of the present invention is characterized in that an original signal having a complex signal which is a multi-channel and cyclic signal measured from one phenomenon is processed by using the time domain high-speed non-linear state space projection method so as to estimate a noise in the original signal and subtract the estimated noise from the original signal, thereby separating the signal to be measured in the original signal as a non-linear signal even when the S/N ratio is low.

EMBODIMENTS

In the following, embodiments of the present invention will be described in detail.

Figure 1:
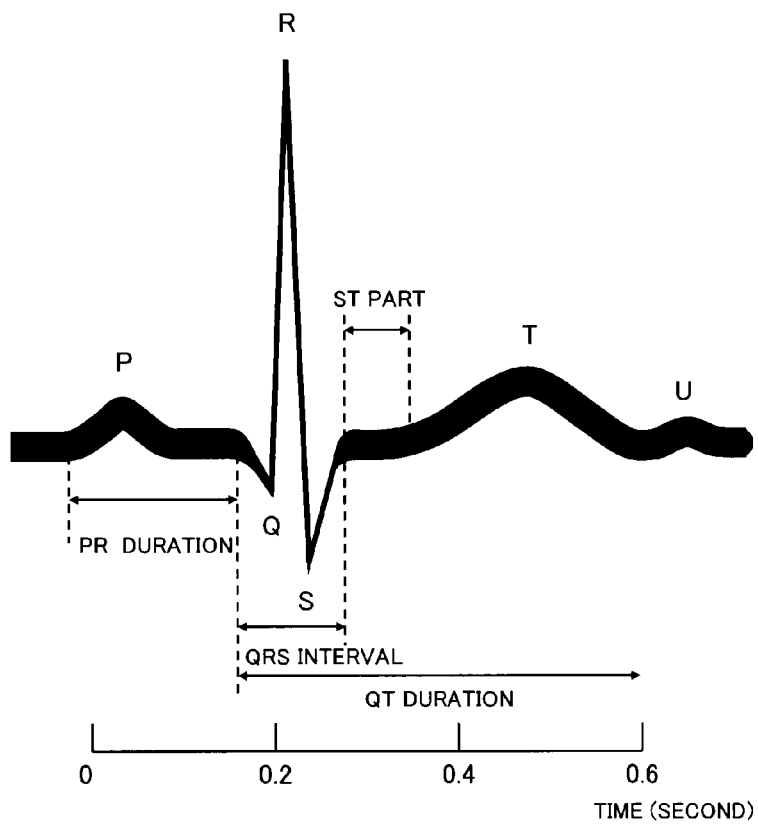
FIG. 1 shows a fundamental waveform on an electrocardiogram.
Figure 2:
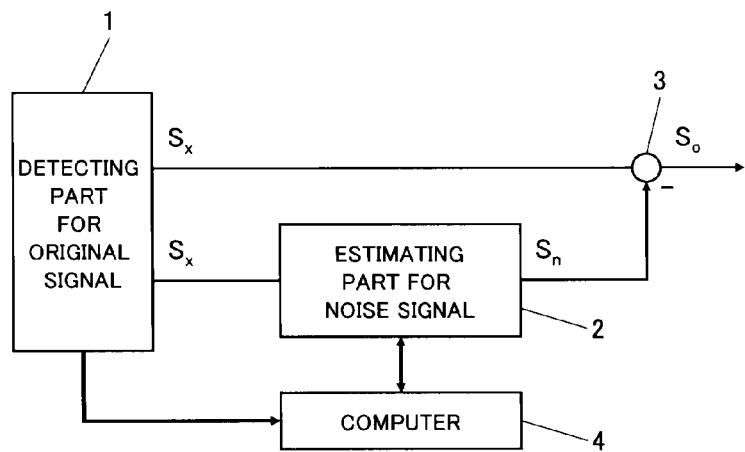
FIG. 2 is a schematic diagram of non-linear signal separation system by using the non-linear state space projection method according to the first embodiment of the present invention.

FIG. 2 is a schematic diagram of non-linear signal separation system by using non-linear state space projection method according to the first embodiment of the present invention.

In this figure, Sx is an original signal, Sn is an estimated noise signal, So is a signal to be measured, 1 is a detecting part for the original signal having a complex signal which is a multi-channel and cyclic signal measured from one phenomenon, 2 is an estimating part for the noise signal Sn (which is a signal other than a signal to be measured) in the original signal Sx, wherein the noise in the original signal is estimated by performing a calculation of cyclic summation average in cooperation with a computer 4 by using the time domain high-speed non-linear state space projection method (Fast Non-linear State Space Projection in time domain; FNSSP in TD) described above. 3 is a subtracting part which subtracts the estimated noise Sn from the original signal Sx. In this subtracting part 3, the noise Sn is removed from the original signal Sx, thereby separating the signal to be measured So in the original signal Sx as a non-linear signal even when the S/N ratio is low.

This separation method is applicable to biological signals such as an electrocardiogram signal, a functional MRI signal, a brain wave signal and so on. It is also applicable to technological measurement data if the data has a cyclic signal.

Figure 3:
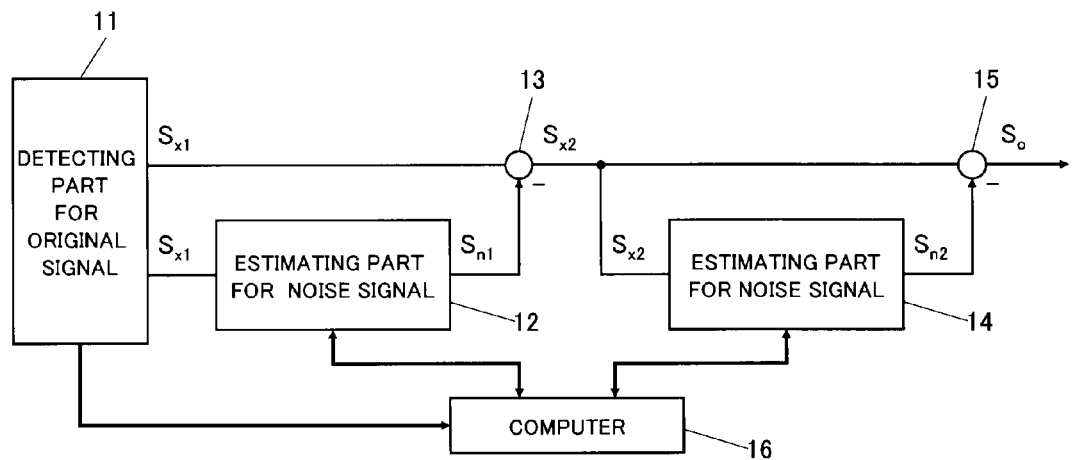
FIG. 3 is a schematic diagram of non-linear signal separation system by using non-linear state space projection method according to the second embodiment of the present invention.

FIG. 3 is a schematic diagram of non-linear signal separation system by using non-linear state space projection method according to the second embodiment of the present invention.

In this figure, Sx1 is an original signal of the first stage, Sn1 is an estimated noise signal of the first stage, Sx2 is an original signal of the second stage, Sn2 is an estimated noise signal of the second stage, So is a signal to be measured, 11 is a detecting part for the original signal having a complex signal which is a multi-channel and cyclic signal measured from one phenomenon, 12 is an estimating part for the noise signal Sn1 of the first stage in the original signal Sx1 of the first stage, wherein the noise in the original signal is estimated by performing a calculation of cyclic summation average in cooperation with a computer 16 by using the time domain high-speed non-linear state space projection method (FNSSP in TD) described above. 13 is a subtracting part which subtracts the estimated noise Sn1 of the first stage from the original signal Sx1 of the first stage. In this subtracting part 13, the noise signal Sn1 of the first stage is removed from the original signal Sx1 of the first stage, and the original signal Sx2 of the second stage is output. 14 is an estimating part for the noise signal Sn2 of the second stage in the original signal Sx2 of the second stage, wherein the noise in the original signal is estimated by performing a calculation of cyclic summation average in cooperation with a computer 16 by using the time domain high-speed non-linear state space projection method (FNSSP in TD) described above. 15 is a subtracting part which subtracts the estimated noise Sn2 of the second stage from the original signal Sx2 of the second stage. In this subtracting part 15, the noise signal Sn2 of the second stage is removed from the original signal Sx2 of the second stage, thereby separating the signal to be measured So in the original signal Sx2 of the second stage as a non-linear signal.

This embodiment is configured to remove a noise twice as described above, and is suitable to be applied to the case of separating biological signals, especially an electrocardiogram signal of a fetus in a mother's body as described in the following.

Figure 4:
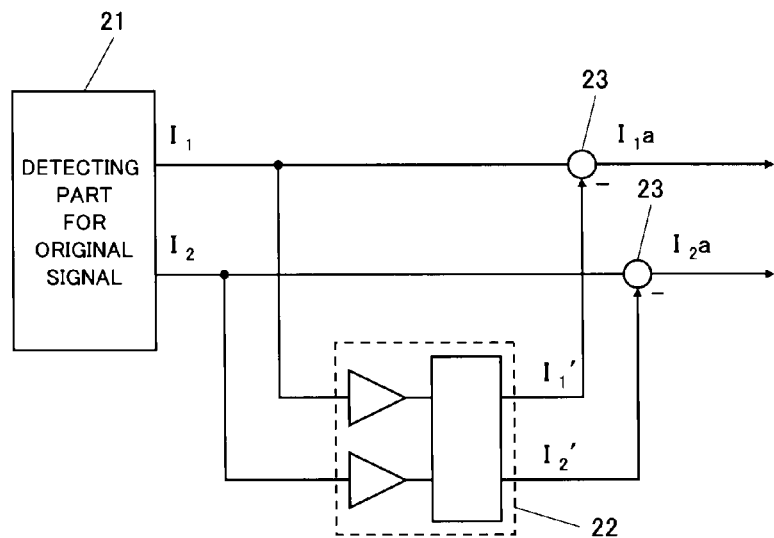
FIG. 4 is a schematic diagram of non-linear signal separation system by using the non-linear state space projection method according to the third embodiment of the present invention in the case of having a 2 channel complex signal.

FIG. 4 is a schematic diagram of the non-linear signal separation system by using the non-linear state space projection method in the case of having a 2 channel complex signal according to the third embodiment of the present invention.

In this figure, 21 is a detecting part for the original signal which has a 2 channel complex signal $I_1$, $I_2$. 22 is an estimating part for the noise signal (including a computer). 23 is a subtracting part which subtracts the noise signal intensity $I_1'$, $I_2'$ calculated from the original signal $I_1$, $I_2$. In this subtracting part 23, the calculated noise signal intensity $I_1'$, $I_2'$ are subtracted from the original signal $I_1$, $I_2$, and the signal to be measured $I_1a$, $I_2a$ are output. Here, the estimating part for the noise signal estimates the noise in the original signal by performing a calculation of cyclic summation average in cooperation with a computer by using the time domain high-speed non-linear state space projection method (FNSSP in TD) described above.

Figure 5:
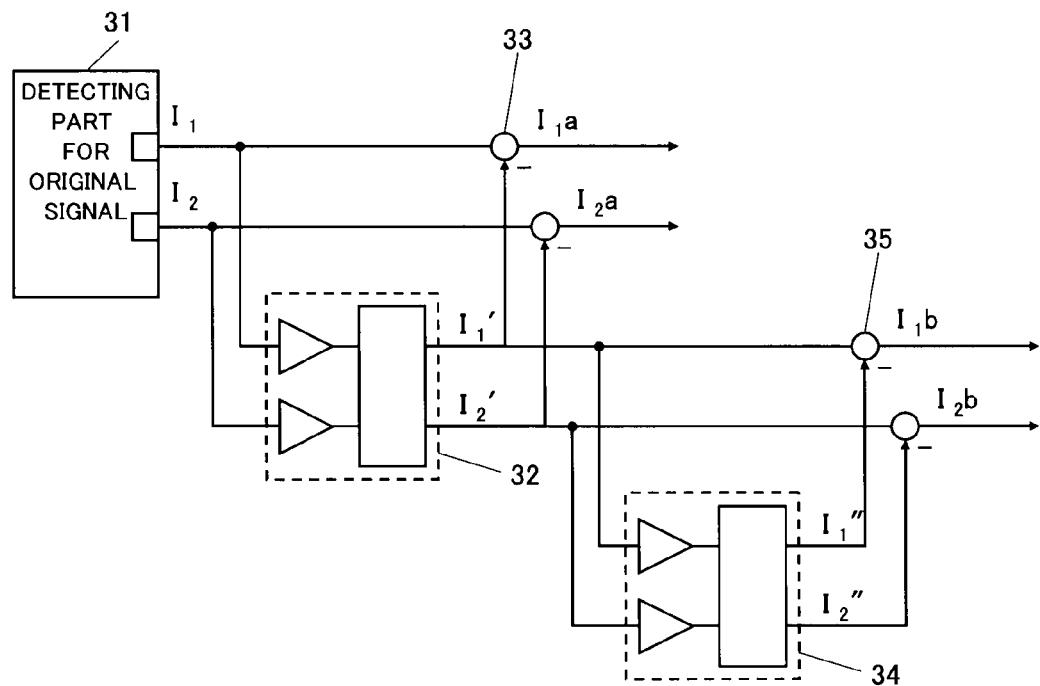
FIG. 5 is a schematic diagram of non-linear signal separation system by using the non-linear state space projection method according to the fourth embodiment of the present invention in the case of having an n channel complex signal.

FIG. 5 is a schematic diagram of the non-linear signal separation system by using the non-linear state space projection method in the case of having an n-dimensional channel complex signal according to the fourth embodiment of the present invention.

In this figure, 31 is a detecting part for the original signal which have a 2 channel complex signal $I_1$, $I_2$. 32 is an estimating part for the noise signal of the first stage. 33 is a subtracting part which subtracts the calculated noise signal intensity $I_1'$, $I_2'$ of the first stage from the original signal $I_1$, $I_2$. In this subtracting part 33, the calculated noise signal intensity $I_1'$, $I_2'$ of the first stage are subtracted from the original signal $I_1$, $I_2$, and the original signal $I_1a$, $I_2a$ of the second stage are output. Furthermore, 34 is an estimating part for the noise signal of the second stage, wherein the noises $I_1''$, $I_2''$ are removed from the original signal $I_1$, $I_2$ of the second stage, and then signal to be measured $I_1b$, $I_2b$ are obtained. Here, each of the estimating part for the noise signal estimates the noise in the original signal by performing a calculation of cyclic summation average in cooperation with a computer by using the time domain high-speed non-linear state space projection method (FNSSP in TD) described above.

Figure 6:
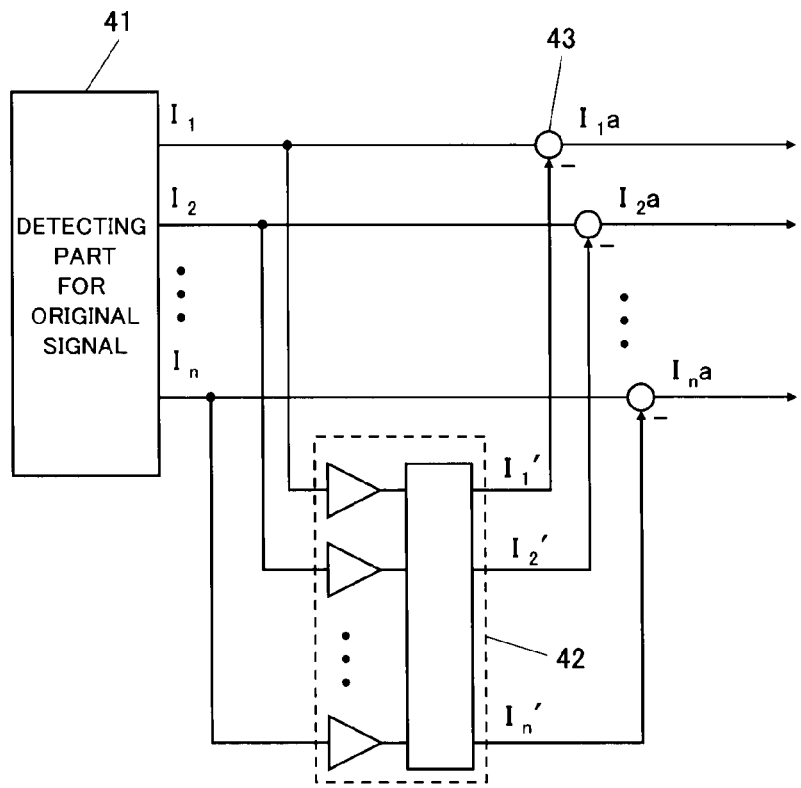
FIG. 6 is a schematic diagram of non-linear signal separation system by using the non-linear state space projection method according to the fifth embodiment of the present invention in the case of having an n channel complex signal.

FIG. 6 is a schematic diagram of the non-linear signal separation system by using non-linear state space projection method in the case of having an n-dimensional channel complex signal according to the fifth embodiment of the present invention.

In this figure, 41 is a detecting part for the original signal which have an n channel complex signal $I_1, \ldots I_n$. 42 is an estimating part for the noise signal $I_1', \ldots I_n'$ of the n channel. 43 is a subtracting part which subtracts the calculated noise signal intensity $I_1', \ldots I_n'$ of the n channel from the original signal $I_1, \ldots I_n$. In this subtracting part 43, the calculated noise signal intensity $I_1', \ldots I_n'$ of the n channel are subtracted from the original signal $I_1, \ldots I_n$, and then the signal to be measured $I_1a, \ldots I_na$ are obtained. Here, the estimating part for the noise signal estimates the noise in the original signal by performing a calculation of cyclic summation average in cooperation with a computer by using the time domain high-speed non-linear state space projection method (FNSSP in TD) described above.

Moreover, the estimating part for the noise signal may comprise a part of cyclic calculation/processing and cyclic summation average calculation and a part of calculation of the noise signal intensity by using the principal component analysis.

A cyclic signal of the present invention includes, as described above, biological signals such as an electrocardiogram signal, a functional MRI signal, a brain wave signal. A technological measurement data is also included if it is a cyclic signal.

In other words, the present invention can be applied to any case where the original signal can be restored accurately by removing the noise while maintaining the dynamical structure.

For the case of a multiple and cyclic data, (1) cyclic data is shifted by one cycle and superposed on the original one. This process is carried out up to several of periods until the summation average becomes stable, for example up to 10 cycles or more. (2) Summation averages are calculated by the superposed data. (3) Scatter from the average is plotted (here, in one dimension). (4) Data processing is carried out in another channel according to the procedure (1) to (3) described above. (5) The processed data for all channels are plotted as a multi-dimensional figure. (6) Calculation is performed to obtain a noise at each data point by performing the principal component analysis for the scatter of the noise in the multi-dimensional plane at each time. (7) Removing the calculated noise from the original data to obtain the signal. The procedures (3) and (4) described above is performed to obtain variation from probability distribution. Since this method performs NSSP in time domain and can perform data processing with high speed, it can be called time domain high-speed non-linear state space projection method (FNSSP in TD) described above.

As an application example of the present invention, a detailed description will be given in the following on the extraction of a fetal electrocardiogram using the time domain high-speed non-linear state space projection method, which is a novel non-linear filtering method to extract a fetal electrocardiogram from a multi-channel signal containing a large amount of noise detected from an abdominal wall of a mother's body.

This method is essentially based on the conventional non-linear state space projection method (NSSP method) (See Non-Patent Document 1 described above.). This conventional method is a method to separate signals mixed with each other non-linearly. But at the same time, this conventional method need several complex conditions and limitations such as setting an appropriate neighborhood and time delay of the state space. Therefore as described above, this conventional method need a large amount of time for calculation. Since the time domain high-speed non-linear state space projection method according to the present invention does not require these conditions, a calculation speed can be 30 times higher than that of the conventional method. By using the method of the present invention, an on-line recording of the electrocardiogram signal component from a fetus has successfully achieved, demonstrating the usefulness of this fetal electrocardiogram observation method to a clinical application.

By the way, although several novel studies have been reported so far concerning the fetal electrocardiogram observation method such as this, the fetal electrocardiogram (ECG) is not used so often in the clinical application. This is due to the difficulty in extracting the fetal electrocardiogram, which is caused by small amplitude of a signal from a fetus, mixing of an electrocardiogram of a fetal with that of a mother's, big background noises such as skin potential, an electromyogram of the mother's body and an uterus electromyogram (See Non-Patent Documents 2, 3, 4, 5 and 6 described above.).

Furthermore, an electrocardiogram signal has a three dimensional structure, and the shadow of the electrocardiogram signal projected to derive the space is non-linearly mixed with multiple, noisy signals detected from the abdominal wall of the mother's body. Almost all of the conventional methods proposed so far are based on linearity of the mixed original signal and the mixing means of these signals such as a mixing matrix. Therefore, it is not possible to perfectly separate a non-linear signal such as an electrocardiogram of a mother's body and a fetal electrocardiogram by using these linear methods.

The time domain high-speed non-linear state space projection method (FNSSP in TD) will be described here, which is a new method to extract non-linearly a fetal electrocardiogram from a mixed abdominal signal.

The method of the present invention is essentially based on the non-linear state space projection method (NSSP), but does not require complicated conditions such as an appropriate neighborhood or a time delay coordinate. Furthermore, the usefulness of the FNSSP in TD is demonstrated by a practical application to clinical data.

The time domain high-speed non-linear state space projection method (FNSSP in TD) will be described in detail in the following.

Here, the state space is defined and a theoretical concept extracted from the NSSP will be explained.

(Definition of State Space)

When a time sequence $x_n$ (n=1, 2, ..., N) is given from a dynamic system, and if the time sequence is buried in the multi-dimensional metric space M which satisfies the following three conditions, M is referred to as a state space of the time sequence.

(1) M is a multi-dimensional probability region metric space. The time sequence is buried in this space and a model orbit is present in this space.

(2) A neighborhood of each point on the model orbit (or trajectory) is defined as a hyperplane having the extra dimension of the model orbit.

(3) The probability structure of the neighborhood is defined only by the point on the model orbit.

(Condition of the State Space of the Time Sequence to Form Natural Model Orbit.)

When the state space satisfies recurrent characteristics of the orbit, the state space of the time sequence forms a natural model orbit.

Definition of Recurrent Characteristics:

When a trajectory passes repeatedly through a neighborhood $N_{r0}$ of an arbitrary point $x_{r0}$ on the trajectory, the trajectory which is a trajectory of the time sequence buried in the state space is considered to have recurrent characteristics. That is, for a time sequence $(t_1, t_2, \ldots, t_m)$, points $x_{t1}$, $x_{t2}, \ldots, x_{tm}$ is present within the neighborhood $N_{r0}$. The trajectory is assumed to recur to the neighborhood as many times as appropriate to calculation.

A model orbital point $m_{r0}$ is obtained as an average between points within each neighborhood $N_{r0}$.

(Time Domain High-Speed Non-Linear State Space Projection Method)

An m dimensional vector time sequence $\vec{\chi}_n$ (n=1, 2, ..., N) is assumed to be a cyclic, or approximately cyclic vector time sequence having the recurrent characteristics. Here, $\vec{\chi}_n$ (n=1, 2, ..., N) is expressed as $\vec{\chi}_n = \vec{S}_n + \vec{r}_n$ (n=1, 2, ..., N), in which $\vec{S}_n = \vec{\chi}_n - \vec{r}_n$ (n=1, 2, ..., N) is a system signal. From the recurrent characteristics, it is assumed that a time sequence $(t_1, t_2, \ldots, t_l)$ exists for an arbitrary time $t_1$ and $\vec{\chi}_n$ (n=1, 2, ..., N) has the same probability structure recurrently in the range $[t_i, t_{i+1}]$ (i=1, 2, ..., l−1). On the other hand, the state space including the time axis of the m dimensional vector time sequence $\vec{\chi}_n$ is defined as $(\vec{\chi}_n, t)$ in the m+1 dimensional Euclidean space. Therefore, the trajectory of this system in this state space can be described as $\{(\vec{\chi}_n, t-t_i); t \in [t_i, t_{i+1}] (i=1, 2, \ldots, l-1)\}$. The neighborhood of the point $(\vec{\chi}_{r0}, t_0)$ at time $t=t_0$ is defined as a hyperplane $t=t_0$ in the m+1 dimensional space, and the point $(\vec{m}_r, t_0)$ on the model orbit can be defined as an average signal of points $(\vec{\chi}_n, t_0)$ within the neighborhood. From the assumption of the recurrent characteristics, the probability structure of the noise $(\vec{\chi}_{r0} - \vec{m}_{r0}, t_0)$ at time $t=t_0$ can be analyzed (See Non-Patent Document 1 described above.) (Refer to FIG. 7.).

Figure 7:
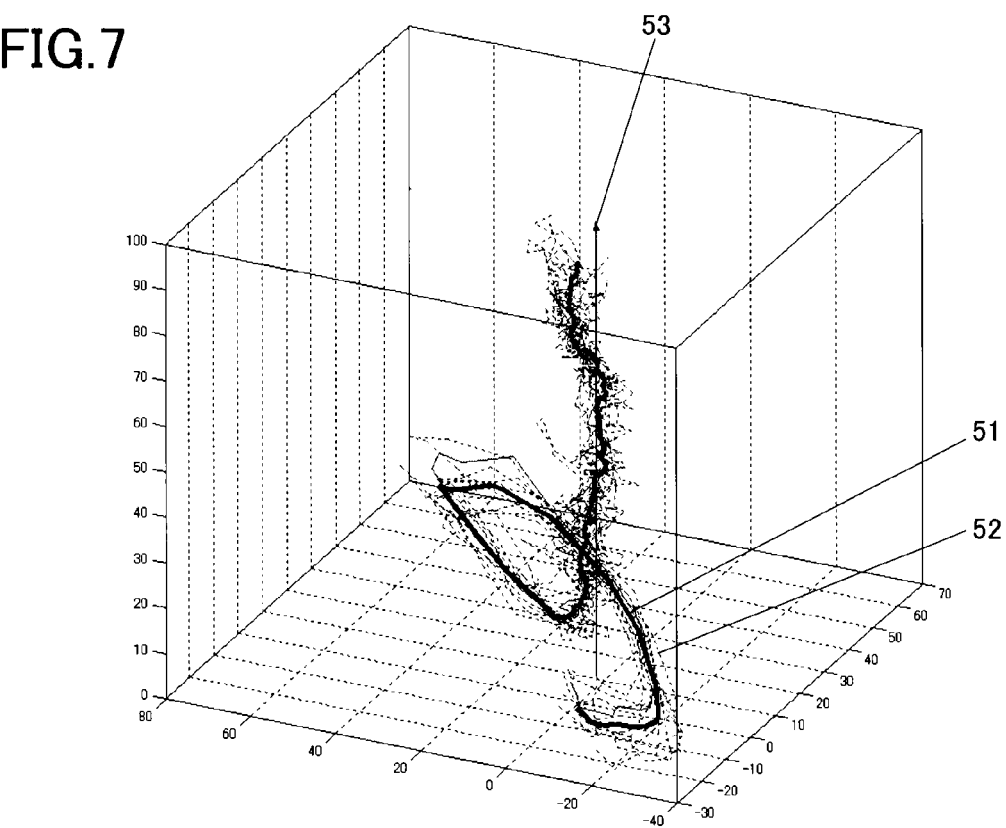
FIG. 7 illustrates a state space for a time sequence $x_n$ of the m-dimensional vector of the present invention.

FIG. 7 shows the state space of the m dimensional vector time sequence $\vec{\chi}_n$, and dotted lines show trajectories 51 $\{(\vec{\chi}_n, t); t \in [t_i, t_{i+1}] (i=1, 2, \ldots, l-1)\}$ of the system. A thick solid line indicates the model orbit $(\vec{m}_{r0}, t_0)$ 5 2 of the time sequence, which is an average of the space points $(\vec{\chi}_n, t)$ at a fixed value t. 53 is a time axis.

Here, the data were obtained from 14 electrodes. Ten electrodes including one reference electrode out of the 14 electrodes are disposed on the abdominal part, one electrode on the right chest, and remaining three including a ground electrode on the back of the mother's body. Twelve channel data recorded between the two terminals were sampled every 1 ms with 16 bit resolution (1 kHz sampling), and a bandpass filter (1 to 100 Hz FIR (Finite Impulse Response) filter) was used.

Figure 8:
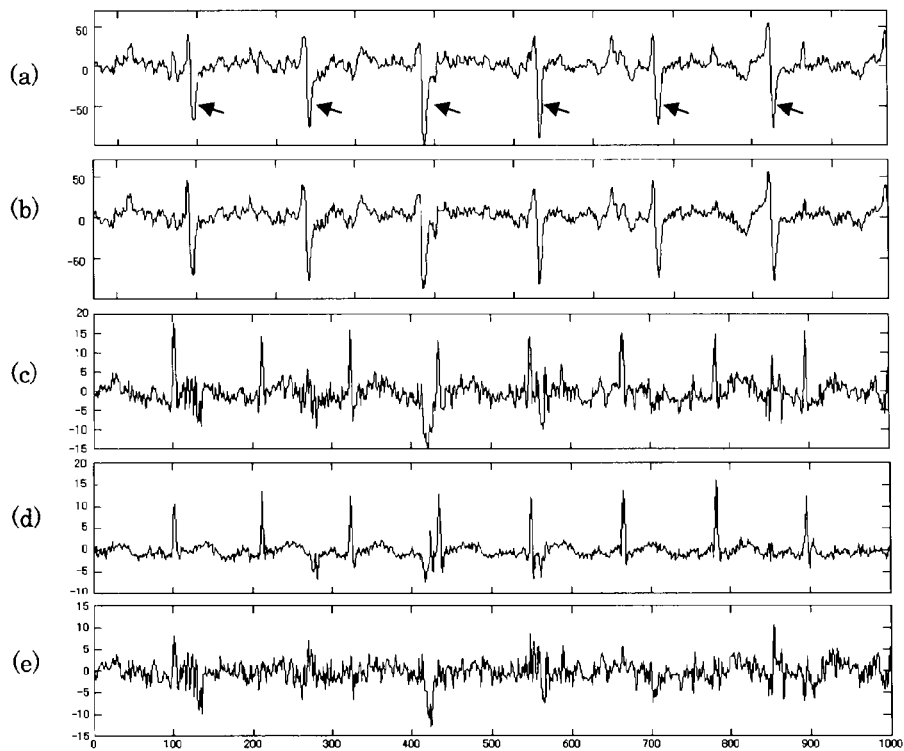
FIG. 8 illustrates an extracted result of a fetal electrocardiogram signal according to the experiment of the present invention.

FIG. 8 shows the result extracted at the second stage of the experiment of the present invention, illustrating a fetal electrocardiogram signal extracted at a time interval of 4 second. FIG. 8(a) shows an abdominal signal recorded at the second stage of the experiment, wherein arrows indicate an electrocardiogram signal of the mother's body. A fetal electrocardiogram signal is hardly recognized. FIG. 8(b) shows an extracted electrocardiogram signal of the mother's body. FIG. 8(c) shows a signal obtained by subtracting the electrocardiogram signal of the mother's body shown in FIG. 8(b) from the abdominal signal shown in FIG. 8(a). Although the obtained signal includes both a fetal electrocardiogram signal and a noise, it clearly shows the presence of the fetal electrocardiogram signal in this sequence. FIG. 8(d) shows the extracted fetal electrocardiogram signal. In this figure, P wave and T wave can be seen. FIG. 8(e) shows a noise component.

Figure 9:
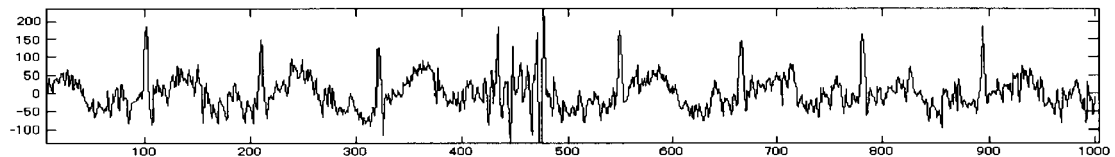
FIG. 9 shows a signal recorded by attaching electrodes directly on a head of a fetus after birth.

Here the FNSSP in TD method was applied twice; in an electrocardiogram of a mother's body was removed for the first time, and a fetal electrocardiogram was extracted for the second time. By using the method of the present invention, extraction of the fetal component was succeeded by removing the signal of the mother's body even when the fetal electrocardiogram component was not observed in the measured signal. By applying the FNSSP in TD method twice (See FIG. 8), the structure of the fetal electrocardiogram appeared. By comparing with the signal recorded by directly applying electrodes to the head of the fetus at the birth, it can be understood that a stable structure is observed by using the FNSSP in TD method (See FIG. 9). The signal of FIG. 9 contains noise.

A comparison of the parameters and the calculation speed between the conventional NSSP method and the method of the present invention is as follows. When the calculation parameters of the conventional NSSP method are set for a sampling rate to be 250 Hz, for a shifting time of the state space to be 4 msec, for a dimension of the state space to be 11, and for the neighborhood in the Poincare map of the attractor orbit to be 13 mV, the calculation time required for data of a phenomenon of time duration of 10 seconds is about 6 hours by using the algorithm just as proposed by Richter, and 6 minutes and 41 seconds by using a simplified method in which the attractor calculation is performed on the time axis in advance.

In contrast, in the case of the method of the present invention, wherein the calculation parameters were set such that the number of repetition was 64, a dimension of the state space was 4 (3 spatial dimensions plus time), the calculation time required to process data with time duration of 10 seconds which is equal to that of the conventional NSSP method was only 3 seconds. This demonstrates that the calculation speed of the present invention is overwhelmingly higher than that of the conventional method, and at the same time demonstrates the feasibility of an on-line processing due to calculation time which is shorter than the time of the phenomenon to be measured.

Furthermore, the present invention is not limited to the embodiments described above, but many modifications and variations are possible on the basis of the essence of the present invention. Those modifications and variations are not excluded from the scope of the present invention.

INDUSTRIAL APPLICABILITY

The non-linear signal separation method by using the non-linear state space projection method according to the present invention is suitable to separate noise signals mixed non-linearly and to extract the signal to be measured, and development of application toward an industry including non-linear signal processing technology is expected.

The invention claimed is:

1. A method of separating non-linear signals using non-linear state space projection in the time domain, the method comprising:
   (i) detecting a first channel of an original signal that is complex and cyclic;
   (ii) shifting the original signal by at least one cycle and superimposing the shifted signal on the original signal to obtain a further signal;
   (iii) repeating step (ii) for further periods of the original signal until a summation average of the further signals is stable;
   (iv) repeating steps (i) to (iii) for at least one other channel of the original signal;
   (v) calculating data points of the further signals for all processed channels in a multi-dimensional plane;
   (vi) performing principle component analysis to calculate noise in the multi-dimensional plane at each data point; and
   (vii) removing the calculated noise from the original signal to obtain a non-linear cyclic signal to be measured.

2. The method according to claim 1, wherein the detecting step comprises detecting the original signal, which includes a biological signal, wherein the non-linear cyclic signal to be measured is the biological signal.

3. The method according to claim 2, wherein the biological signal is an electrocardiogram signal.

4. The method according to claim 3, wherein the electrocardiogram signal is an electrocardiogram signal of a fetus in a mother's body.

5. The method according to claim 4, wherein steps (i) to (vii) are carried out for a first time with the noise that is removed from the original signal equating to an electrocardiogram signal of the mother's body, and the steps (i) to (vii) are carried out a second time to remove other noise from the processed original signal to obtain the electrocardiogram signal of the fetus.

6. The method according to claim 2, wherein the biological signal is a functional MRI signal.

7. The method according to claim 2, wherein the biological signal is a brain wave signal.

8. The method according to claim 1, wherein the detecting step comprises detecting the original signal, which comprises a sound signal arising from a defect in a rotating machine, and wherein the non-linear cyclic signal to be measured is the sound signal arising from the defect in the rotating machine.

9. The method according to claim 1, wherein step (v) comprises calculating the data points of the further signals as the summation average and displacement of the summation average in the multi-dimensional plane.

10. The method according to claim 9, wherein step (vi) comprises performing the principle component analysis of the displacement.

* * * * *